(12) United States Patent
Vargas Fonseca

(10) Patent No.: US 10,260,650 B2
(45) Date of Patent: Apr. 16, 2019

(54) FLOW-CONTROL VALVE ARRANGEMENTS AND IMPROVEMENTS

(71) Applicant: ZAMMI INSTRUMENTAL LTDA, Duque de Caxias, RJ (BR)

(72) Inventor: Luiz Henrique Vargas Fonseca, Duque de Caxias (BR)

(73) Assignee: ZAMMI INSTRUMENTAL LTDA, Duque de Caxias, RJ (BR)

( * ) Notice: Subject to any disclaimer, the term of this patent is extended or adjusted under 35 U.S.C. 154(b) by 0 days.

(21) Appl. No.: 15/023,607

(22) PCT Filed: Oct. 18, 2013

(86) PCT No.: PCT/BR2013/000429
§ 371 (c)(1),
(2) Date: Mar. 21, 2016

(87) PCT Pub. No.: WO2015/024081
PCT Pub. Date: Feb. 26, 2015

(65) Prior Publication Data
US 2016/0208940 A1    Jul. 21, 2016

(51) Int. Cl.
*F16K 15/14* (2006.01)
*A61M 5/168* (2006.01)
*A61M 39/24* (2006.01)

(52) U.S. Cl.
CPC ....... *F16K 15/144* (2013.01); *A61M 5/16804* (2013.01); *A61M 39/24* (2013.01); *A61M 2039/2433* (2013.01); *A61M 2039/2466* (2013.01); *F16K 15/145* (2013.01)

(58) Field of Classification Search
CPC ............................ F16K 15/144; F16K 15/145; A61M 5/16804; A61M 2039/2433

USPC ......................................... 137/843, 852, 859
See application file for complete search history.

(56) References Cited

U.S. PATENT DOCUMENTS

| | | | | |
|---|---|---|---|---|
| 2,758,609 | A * | 8/1956 | Dickert | F16K 15/144 137/512 |
| 3,084,707 | A * | 4/1963 | Frye | F15B 13/04 137/102 |
| 7,484,526 | B2 * | 2/2009 | Zelson | F16K 15/144 137/515.7 |
| 2008/0058720 | A1 | 3/2008 | Spohn et al. | |

FOREIGN PATENT DOCUMENTS

| | | |
|---|---|---|
| DE | 202007011811 U1 | 11/2007 |
| EP | 0247824 A2 | 12/1987 |
| EP | 1099455 A2 | 5/2001 |

* cited by examiner

*Primary Examiner* — P. Macade Nichols
(74) *Attorney, Agent, or Firm* — Nath, Goldberg & Meyer; Joshua B. Goldberg

(57) ABSTRACT

The present invention relates to improvements of valves of the cartwheel type, with receptive arrangements incorporating the valves, which comprise a component of elastomeric material in the form of a cartwheel fastened by means of the external ring to the valve case. The invention comprises a central plug connected by rods to the external ring and, normally, when used in two-way casings (with only one inlet and one outlet), the valve acts as a unidirectional valve. When used in a three-way casing, or a casing with more than three thereof, the valve can act to seal off and let through a flow of fluid on either side of the valve, alternately, depending on the fluid-circulation design choice.

6 Claims, 7 Drawing Sheets

Figure 1 (Prior Art)
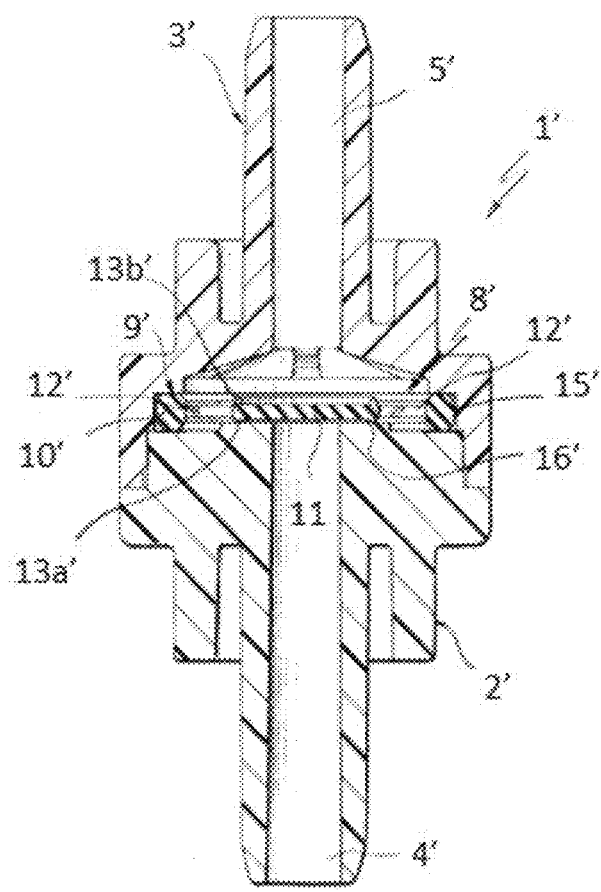
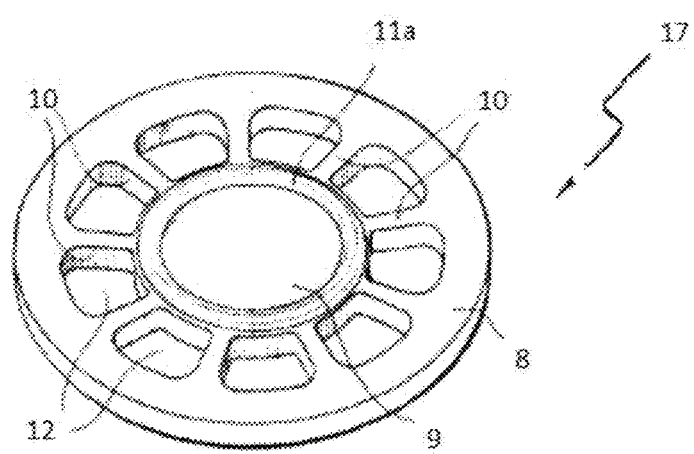

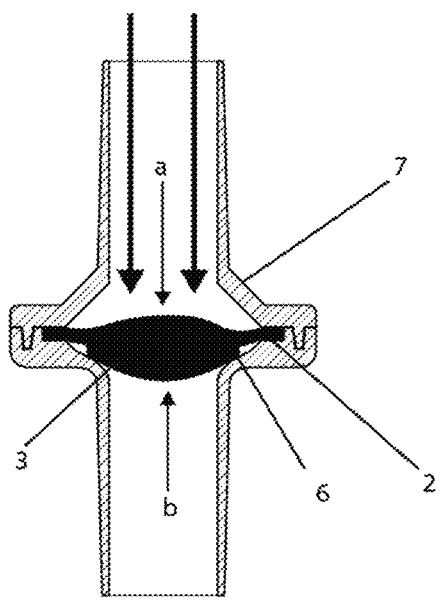
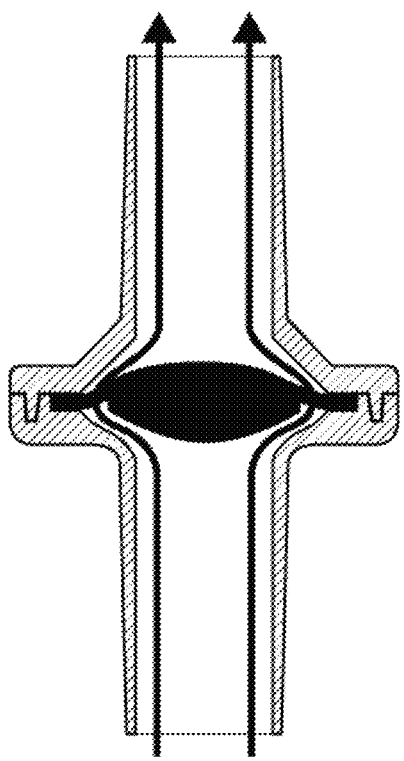
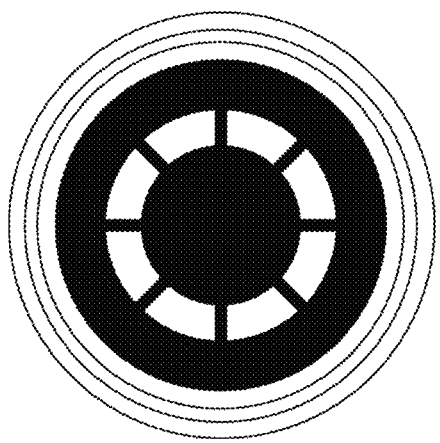

FLOW-CONTROL VALVE ARRANGEMENTS AND IMPROVEMENTS

This is a National Phase Application filed under 35 U.S.C. 371 as a national stage of PCT/BR2013/000429, filed Oct. 18, 2013, the content of which of which is hereby incorporated by reference in its entirety.

FIELD OF THE INVENTION

The present invention refers to a flow-control valve improvement, here called cartwheel-type valve, which is a multifunctional valve that can be used to control flow of both liquid and air, being able to perform different functions depending on the casing where it is mounted.

The valve according to the present invention can be applied in many different areas where a flow control is desirable, such as in medicine or industry, functioning as an anti-reflux one-way valve, or for automatic flow control.

BACKGROUND OF THE INVENTION

Generally, flow-control valves of the cartwheel type are known, as can be seen in the prior art references EP 1 099 455 and EP 0 336 307. Typically, they consist of a piece of silicone, or other elastomeric material, formed with a cartwheel that is fixed by the external ring to the valve casing and thus having freedom to move in only one direction when subjected to pressure. This mobility is typically due to the flexibility of the rods which connect the rim to the plug in the center of the valve. When assembled, with no pressure in the valve inlet, or when the pressure is applied in the opposite direction to the one intended, the valve is supported on the base or focus of the capsule, sealing the inlet and thereby preventing flow in the opposite direction. When pressure is applied in the intended flow direction, the valve moves, allowing the passage of flow between said rods. Therefore, it is configured as a unidirectional valve or anti-reflux valve.

There are some techniques in the market or types of valves that make anti-reflux function, such as, for example, the duckbill valve, umbrella type valve and said valves of the cartwheel type. However, these valves have some deficiencies of structural and functional nature that point to solutions not yet contemplated by the prior art, as commented below.

Duckbill Valve

This type of valve has a structure that favors the accumulation of waste in their inner corners, in addition to generating undesirable turbulence for certain applications, such as those in medicine. Add to that the fact that there is some difficulty to remove the valve inside the air. In addition, this valve has flow restrictions, since the liquid passage area is smaller than the area of the inlet connector. When used with air, it produces sound that can be disturbing depending on the application.

Umbrella Valve

The structure of this valve also favors the accumulation of waste in the corners, also generating undesirable turbulence for applications in medicine, particularly if the fluid is blood. They also have difficulty in extracting it from the inside air, as well as flow restriction, because the liquid passage area is smaller than the area of the inlet connector. If used with air, it produces uncomfortable noise depending on the application.

Cartwheel Valves

This type of valve, as disclosed in prior art documents EP 1 099 455 and EP 0 336 307, because the central plug plan format, also generates accumulation of waste in the inner corners, in addition to the already mentioned undesirable turbulence, especially when the fluid is blood. Furthermore, due to the central plug plan format, if subjected to high suction pressures in the inlet, it can deform and thus allow the passage of flow. Additionally, if it is used in long-term applications, said central plug plan format can suffer deformations that may lead to fluid leaks. Finally, the central plug plan format of the valve limits its work for only one direction of flow, not being possible its application as a three or more-way valves.

Another problem observed in the low control devices of the current state of the art, mainly when used in medicine, such as in hemodynamic and infusion substances to patients where it is necessary to control one or more fluid flows by three or more paths, relates to arrangements used. In general, it relates to flow driver devices consisting of taps, records and manifolds, which require the gauntlets handling to obtain the direction of flow to the desired outlet. Obviously, this handling is not suitable and can even generate problems for due process that the patient is undergoing.

It is, however, an objective of the present invention minimize and even solve the aforementioned problems, through the provision of a flow-control valve of the cartwheel type, with proper constructive characteristics and made of silicone, rubber, flexible PVC or other elastomeric material that meets the necessary flexibility specifications and resistance to valve operation, enabling better adjustments and reliability for characteristics such as opening pressure, maximum flow, flow resistance, biocompatibility, durability, etc.

It is another objective of the present invention to provide a unidirectional flow-control valve of the cartwheel type, with peculiar constructive characteristics so that it can alternatively and selectively as design option, work in both sides of the valve, as a sealing or for passage of fluid flow.

Among the many improvements and advantages that the constructive characteristics of the flow-control valve of the cartwheel type, object of the present invention, can present in relation to those of prior art, stand out:

Better sealing between the plug and the base of the capsule, obtained by the arch-shaped fitting of the plug with the base of the capsule. Thus, the higher the pressure the better the sealing, with no reflux even when the valve deforms with pressure;

Due to the arch format in both sides of the valve, depending on the inner format of the base of the capsule, when in a system or arrangement of three ways or more, it is possible to work with the valve plug sealing or giving passage to the fluid flow, as alternative of chosen inlets and outlets.

Yet another object of the present invention is to provide arrangements with flow-control valves of the cartwheel type, replacing the current flow drivers, so that the operation is fully automatic and safe. Said arrangements in cartwheel-type valves according to the present invention have the following advantages over the current flow drivers:

Fully automatic and safe operation, without the need to turn any gauntlet or device, with no risk of error in the required flow direction;

Low cost, because it is not necessary to use several maneuvering devices simultaneously;

Reduced size in relation to prior art devices.

BRIEF DESCRIPTION OF THE DRAWINGS

The present invention will be described below with reference to the accompanying drawings, that in a schematic and not limited form of its scope, represent:

FIG. 1 illustrates two diagrammatic views of a flow-control valve of the cartwheel type, according to the prior art;

FIG. 5 illustrates a longitudinal sectional view of the cartwheel-type valve mounted in the capsule, with the flow direction with fluid seal according to the present invention;

FIG. 6 illustrates a longitudinal sectional view of the cartwheel-type valve mounted in the capsule, with flow direction to open fluid passage according to the present invention;

FIG. 7 illustrates a top view of the cartwheel-type valve mounted in the capsule according to the present invention;

DETAILED DESCRIPTION OF THE INVENTION

Figure 2:
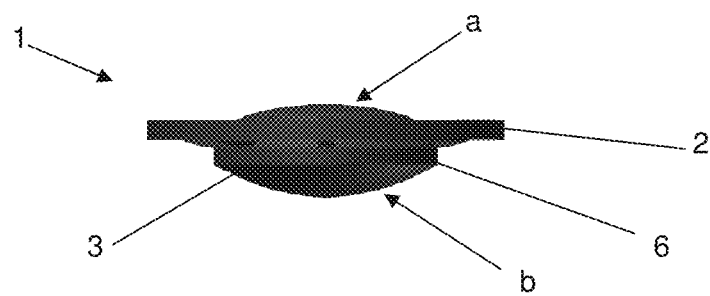
FIG. 2 illustrates a front view of the cartwheel-type valve, according to the present invention.
Figure 3:
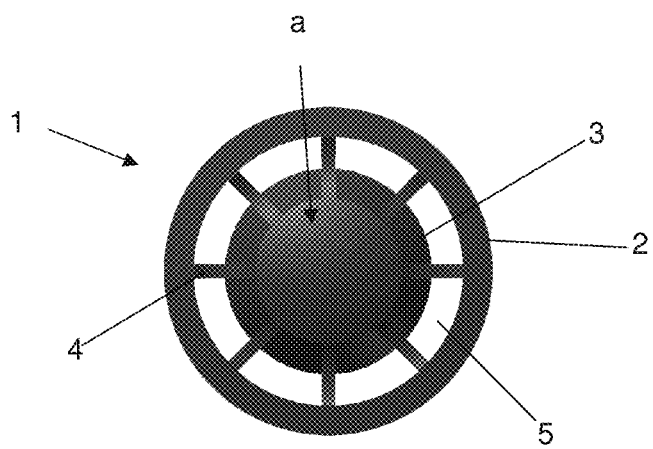
FIG. 3 illustrates a top view of the cartwheel-type valve, according to the present invention.
Figure 4:
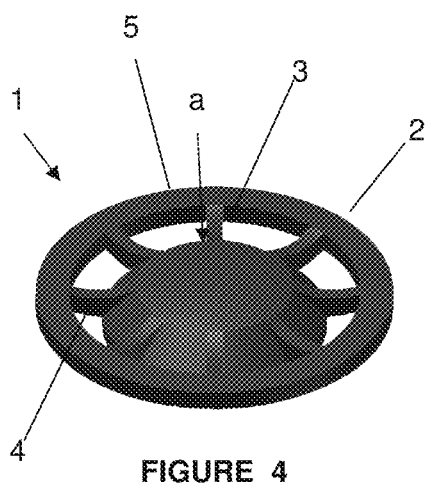
FIG. 4 illustrates a perspective view of the cartwheel-type valve, according to the present invention.

As illustrated in the aforementioned figures, the flow-control valve of the cartwheel type (1) should be made of an elastomeric material having wagon wheel shape which is fixed by the external ring (2) to the valve or capsule (7) casing having the freedom to move in only one direction if mounted as shown in FIGS. 5, 6 and 7 and when subjected to pressure. This possibility is achieved due to the flexibility of the rods (4) connecting the external ring (2) to the central plug (3) forming equidistant openings (5). Said central plug (3) has different configurations for the sides (a) and (b), being the side (a) of arc-shaped contour less prominence than that of the contour of side (b) that also in arc shape, has a steeper contour than the side (a) in addition to revealing a cylindrical extension (6). Due to the massive construction and prominent contours of the central plug (3), the rods (4) has a slight slope portion starting at the limit of circumference of the central plug arc (3) by the side (a) extending to the flat part contiguous to external ring (2).

Figure 8:
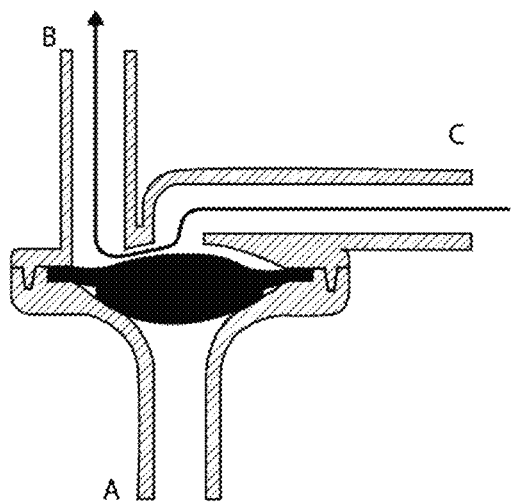
FIGS. 8 and 9 illustrate a longitudinal sectional view of a three-way capsule comprising a cartwheel-type valve, with flow passage and sealing, alternatives by the side (a) or side (b) of the plug according to the fluid inlet option, according to the present invention.
Figure 9:
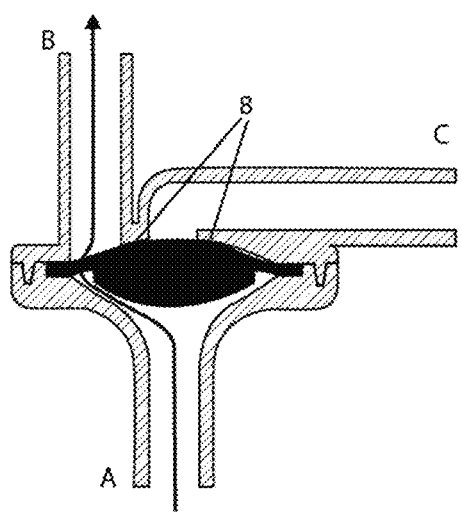
Figure 10:
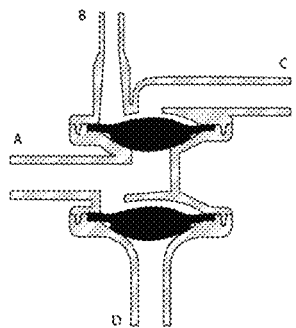
FIGS. 10, 11, 12 and 13 illustrate longitudinal sections of cartwheel-type valve arrangements, with four-way capsules, for different options for the inlet and outlet of fluid, according to the present invention.
Figure 11:
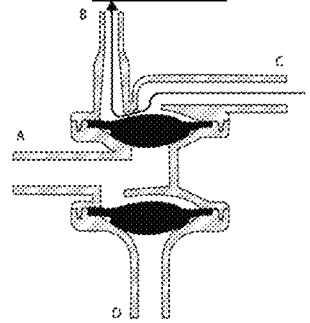
Figure 12:
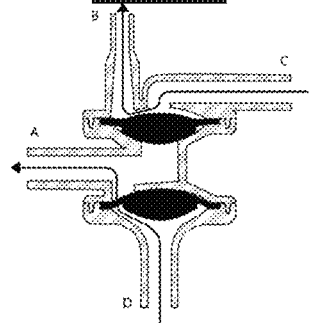
Figure 13:
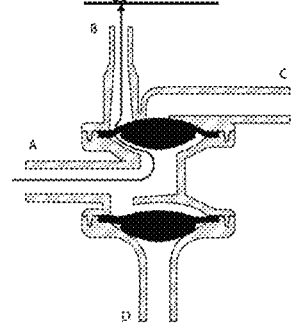
Figure 14:
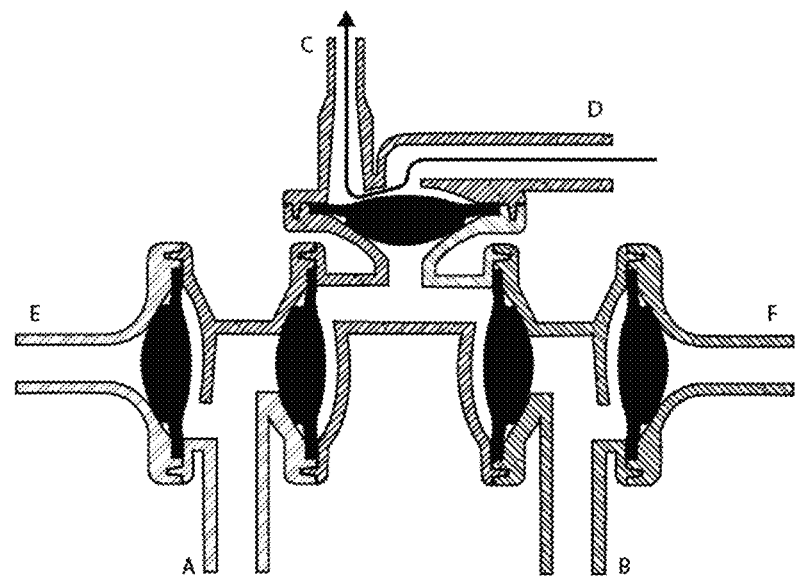
FIGS. 14, 15, 16 and 17 illustrate longitudinal sections of another type of cartwheel-type valve arrangements, with six-way capsules, for different options for the inlet and outlet of fluid, according to the present invention.
Figure 15:
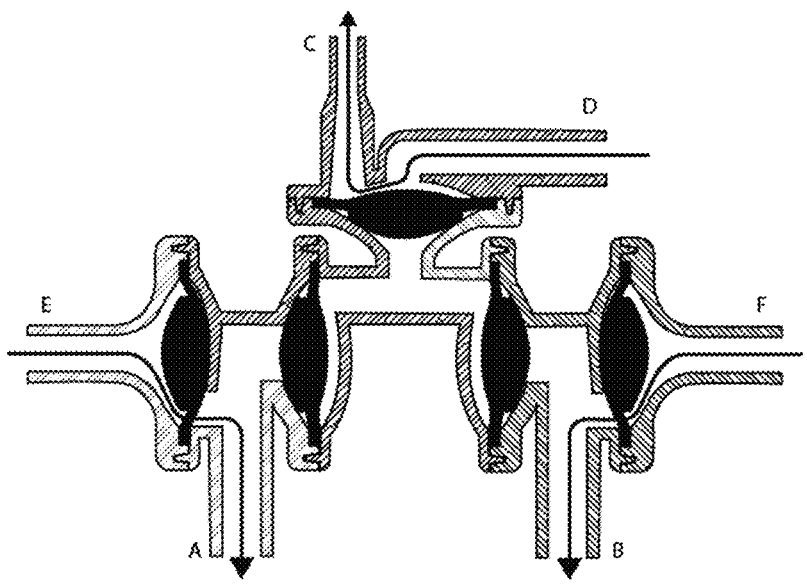
Figure 16:
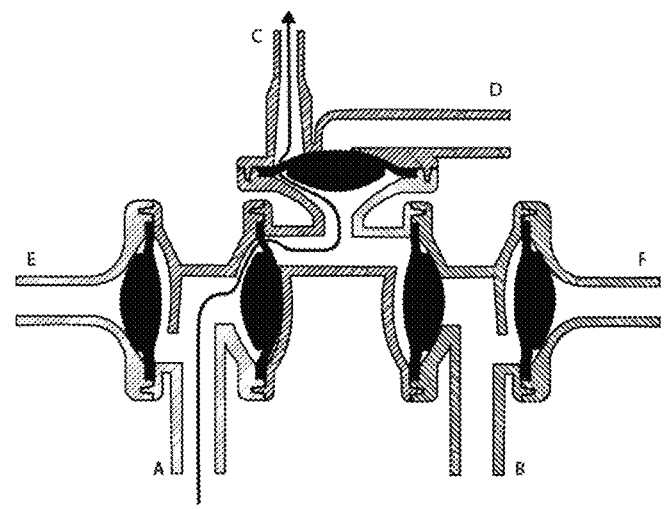
Figure 17:
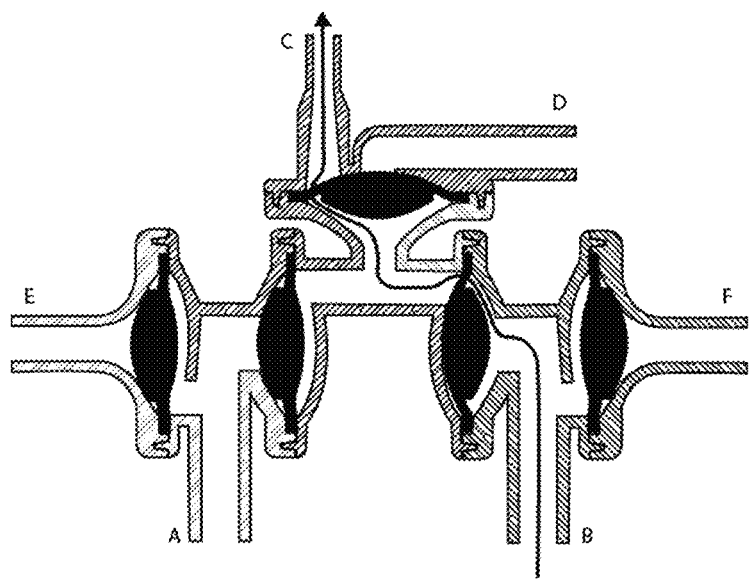

In the cartwheel-type valve thus configured, when working in capsules as a three-way valve, examples of FIGS. 8 and 9, both the side (a) and side (b) of the central plug (3) can exert the passage and sealing function, depending on the choice of flow inlet. FIG. 9 illustrates an example of inlet in (A) and outlet in (B). Thus, the inlet is by the side (a), which normally would not make contact with the focus or base (9) of the capsule, then going to have sealing by the valve seat contact (8) with the base (9) of the capsule also by the side (a). When the choice is inlet in (C) and outlet in (B), as shown in FIG. 8, the cartwheel valve (1) typically will seal by the side (b). It can be seen therefore that the cartwheel-type valve, object of the invention, is perfectly adapted to provide sealing and passage through both sides (a) and (b) of the central plug (3). What will define the seal or not by both sides will be only the construction of the focus or base (9) of the capsule chosen in specific project. Differently, the cartwheel-type valve of the prior art, due to the flat format of the central plug, only allows sealing for only one side (a) or (b).

Thus based on the properties of sealing and passage that the cartwheel valve, object of the present invention, can be carried out by both sides (a) and (b) of the central plug (3), various types of arrangements can be applied to meet the most different flows handling processes commonly required in medical area, thus automating the procedures usually to be run.

Based on this structure of the cartwheel valve object of the invention, examples of possible arrangements, but not limited, are those illustrated in FIGS. 10, 11, 12 and 13, which define a four-way capsule, providing alternatives of fluid flows inlet and outlet as required design. Likewise, arrangements shown in FIGS. 14, 15, 16 and 17 are possible, which comprise a six-way capsule, also providing alternatives of process flow inlet and outlet.

It is noted that in both arrangements exemplified above, the same constructivity of the cartwheel-type valve according to the present invention may alternatively take the proviso of sealing or passage depending on the choice of inlet to be adopted in the process of fluid circulation.

The invention claimed is:

1. A flow-control valve of the cartwheel type, comprising a piece of elastomeric material in wagon wheel format which is fixed by an external ring (2) to a valve casing (7), wherein a central plug (3) is of solid construction and has different constructive configurations for both sides (a) and (b) in the valve, wherein the side (a) has an arc-shaped contour less prominent than an arc-shaped contour of side (b), and the arcshaped contour of side (b) having steeper contour than that of the side (a), but revealing a cylindrical extension (6), wherein rods (4) connecting the central plug (3) to the external ring (2) have a slight slope portion that begins at the limit of a circumference of the central plug arc (3) by the side (a) and extends all the way to a flat part contiguous to the external ring (2), such that a first plane through the limit of the circumference of the central plug arc (3) by the side (a) and a second plane through the flat part contiguous to the external ring (2) are at different levels.

2. The flow-control valves of the cartwheel type according to claim 1 wherein when attached to a three-way or more valve casing, both sides (a) and (b) of the central plug (3) can act as a seal and passage of fluid flow alternatively, wherein sealing of side (a) is performed by a valve seat contact (8) on a base or focus (9) of a capsule.

3. The flow-control valves of the cartwheel type according to claim 1, wherein the flow-control valves are mounted on a four-way valve casing.

4. The flow-control valves of the cartwheel type according to claim 1, wherein the flow-control valves are mounted on a six-way valve casing.

5. The flow-control valves of the cartwheel type, according to claim 3, wherein a valve disposal performs an automatic flow control.

6. The flow-control valves of the cartwheel type, according to claim 4, wherein a valve disposal performs an automatic flow control.

\* \* \* \* \*